United States Patent [19]

Mansfeld et al.

[11] 4,221,651
[45] Sep. 9, 1980

[54] ELECTROCHEMICAL CELL FOR MEASURING HYDROGEN IN METAL

[75] Inventors: Florian B. Mansfeld, Westlake Village, Calif.; David K. Roe, Portland, Oreg.

[73] Assignee: Rockwell International Corporation, El Segundo, Calif.

[21] Appl. No.: 51,771

[22] Filed: Jun. 25, 1979

[51] Int. Cl.³ ............................................. G01N 27/46
[52] U.S. Cl. .............................. 204/195 C; 204/195 F
[58] Field of Search ............. 204/195 R, 195 F, 195 P, 204/195 C, 224 R

[56] References Cited

U.S. PATENT DOCUMENTS

| | | | |
|---|---|---|---|
| 1,739,657 | 12/1929 | Shemitz | 204/224 R |
| 2,463,711 | 3/1949 | Nagle | 204/224 R |
| 2,540,602 | 2/1951 | Thomas et al. | 204/224 R |
| 2,886,497 | 5/1959 | Butler | 204/1 T |
| 4,065,373 | 12/1977 | Martin | 204/195 C |

*Primary Examiner*—T. M. Tufariello
*Attorney, Agent, or Firm*—L. Lee Humphries; Craig O. Malin

[57] ABSTRACT

A cell is provided which utilizes the electrochemical permeation technique to determine the hydrogen content of a metal. The working face of the cell has an opening into a cavity within the cell. A sponge for holding electrolyte fits in the cavity and an anode extends into the cavity. A contact is provided on the working face for contacting the metal being measured. When the cell is held against the metal being measured by the magnet which encloses the cell, a current caused by the oxidation of hydrogen permeating from the metal flows between the anode and the contact electrode. A circuit is provided to measure this hydrogen oxidation current and to calculate the hydrogen content based upon diffusion equations. A seal formed around the opening prevents leakage of electrolyte during the measurement and defines the area being measured. The potential between a special reference electrode positioned in the cavity and the anode is measured to determine if the anode is properly charged and to confirm that sufficient electrolyte is present in the cavity.

5 Claims, 6 Drawing Figures

ELECTROCHEMICAL CELL FOR MEASURING HYDROGEN IN METAL

STATEMENT OF GOVERNMENT INTEREST

The invention herein described was made under a contract with the Department of Defense.

BACKGROUND OF THE INVENTION

1. Field of the Invention

This invention relates to the field of electrochemistry.

2. Description of the Prior Art

Hydrogen atoms can be absorbed into metals such as steels due to corrosion or during pickling, plating, or welding. During these processes, hydrogen may enter the metallic lattice interstitially and permeate throughout the metal. As a result, the ductility of the metal can be reduced greatly, a phenomena known as hydrogen embrittlement.

The amount of hydrogen required to cause embrittlement of high strength steels is in the parts per million range. Vacuum fusion techniques are known for determining the hydrogen content of metals, but these techniques are expensive and require destruction of the part being analyzed. A non-destructive technique based upon measuring the permeation of hydrogen through the metal has been proposed (D. A. Berman, W. Beck, and J. J. DeLuccia in "Hydrogen in Metals", I. M. Bernstein and W. W. Thompson, Editors, ASM (1974), p. 595). According to the Berman et al technique, a "barnacle cell" is attached to the metal. The barnacle cell is the anodic side of a hydrogen permeation apparatus and it utilizes a large non-polarizing electrode to oxidize hydrogen atoms that are electrochemically induced out of the metal. The resulting hydrogen oxidation current is then used to calculate the concentration of hydrogen in the metal part from Faraday's law and from known diffusion equations.

The use of barnacle cells to measure hydrogen in metal parts requires that cup-like cells full of electrolyte be positioned on the metal surface. Additionally, the hydrogen oxidation current must be accurately measured. Until the present invention, such problems have prevented the practical use of hydrogen permeation to measure the hydrogen concentration in metals.

SUMMARY OF THE INVENTION

It is an object of the invention to provide an improved electrochemical cell for measuring the hydrogen concentration in metals.

It is an object of the invention to provide a small portable electrochemical cell for measuring the hydrogen concentration in metals.

It is an object of the invention to provide a portable measurement system which can be used to accurately measure and record the current due to oxidation of hydrogen contained in the test sample.

It is an object of the invention to provide a portable electrochemical cell which can be placed against the surface of a metal part without spilling or leaking electrolyte and used for measuring the hydrogen concentration in the metal.

It is an object of the invention to provide a portable electrochemical cell for measuring the hydrogen concentration in metals, which has means for easily determining if the cell is functioning properly.

According to the invention, the cell is a small insulating body having a cavity for holding electrolyte. The cavity is open on a working face of the cell. A sponge is placed in the cavity for holding the electrolyte, and an elastomeric seal is provided on the working face around the opening in the cavity. The seal defines the area of the metal being measured and helps prevent electrolyte leaking from the sponge and cavity. An anode is positioned inside the cavity adjacent the sponge for maintaining an oxidizing potential on the working face of the cell when it is placed against the metal being measured.

Spring loaded contacts extend from the insulating body of the cell across the working face of the cell and these contacts make electrical contact with the metal being measured. A current-follower electronic circuit is provided between the contacts and the anode so that current caused by the oxidation of hydrogen permeating from the metal can be accurately measured. Faraday's law and the equations defining permeation of hydrogen from metals can then be used to determine the hydrogen content of the metal.

An electronic circuit is also provided for measuring the voltage between the anode and a reference electrode in the cavity. The voltage between the anode and reference electrode is used to confirm that sufficient electrolyte is in the cell and that the anode charge is not depleted.

In a preferred embodiment, the anode and the reference electrode are Ni/NiO electrodes. The seal is a tubular member extending into a cavity and has an elastomeric lip in the plane of the working face for making sealing contact with the metal being measured. A small vent hole and needle valve are provided to vent gas from the cell, particularly when the cell is being positioned against a metal surface.

These and other objects and features of the present invention will be apparent from the following detailed description, taken with reference to the accompanying drawings.

DESCRIPTION OF THE PREFERRED EMBODIMENT

Figure 1:
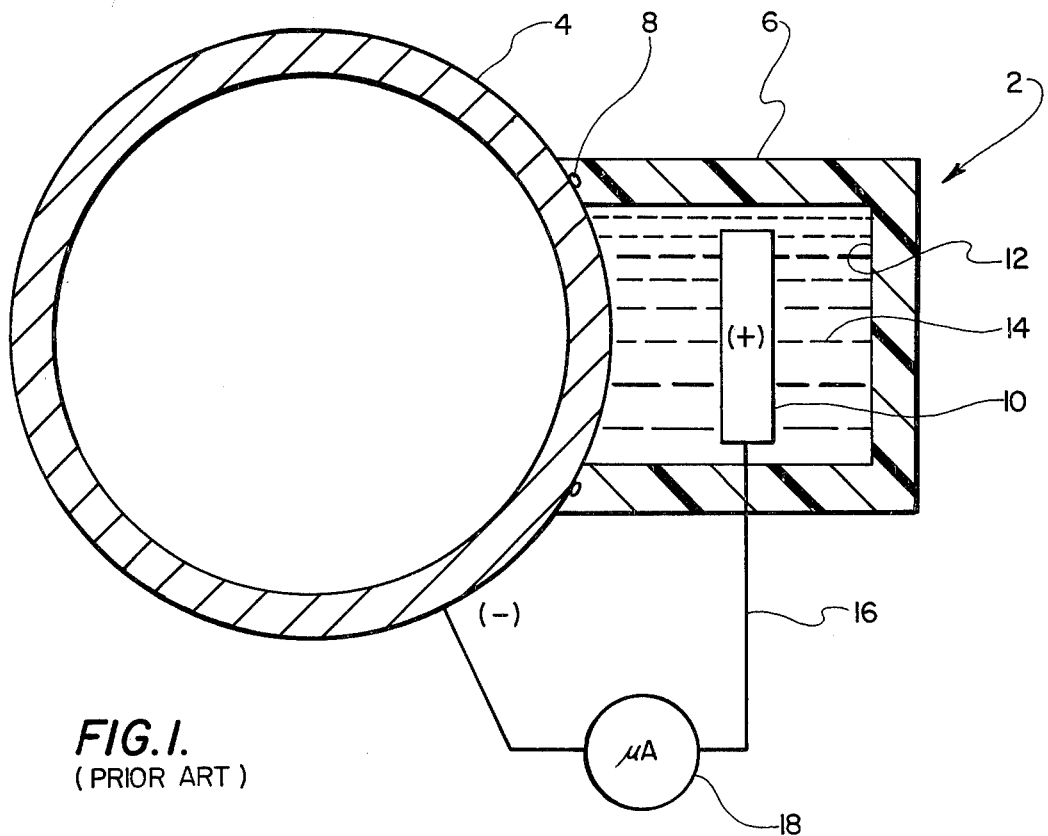
FIG. 1 is a schematic cross-sectional drawing showing the proposed design of a barnacle cell according to the prior art fastened to a pipe.

FIG. 1 shows the proposed design for a prior art cell 2 fastened to a tubular landing gear strut 4 for measuring its hydrogen content. The body 6 of cell 2 is a small cup machined from a block of teflon. The working face of body 6 is machined to fit against strut 4, and is provided with rubber seal 8. An anode 10 of Ni/NiO is provided inside a cavity 12 in body 6. Note that the design in FIG. 1 has never been used experimentally in the field.

To use cell 2, it is filled with a 0.2 N NaOH electrolyte 14. Body 6 is then placed against strut 4 and held tightly in place with a C-clamp or with magnets. Anode 10 oxidizes hydrogen atoms that are electrochemically induced out of metal strut 4, causing current to flow in wire 16 connecting anode 10 to strut 4. A sensitive current measuring meter 18 is used to measure this hydrogen oxidation current. According to Faraday's law, the integration of the hydrogen oxidation current with respect to time can be used to determine the amount of hydrogen in the metal being measured. However, a better procedure is to obtain the concentration of hydrogen from the shape of the current time transient. This known method is explained later as applied to the specific electrical chemical cell of the present invention.

Figure 2:
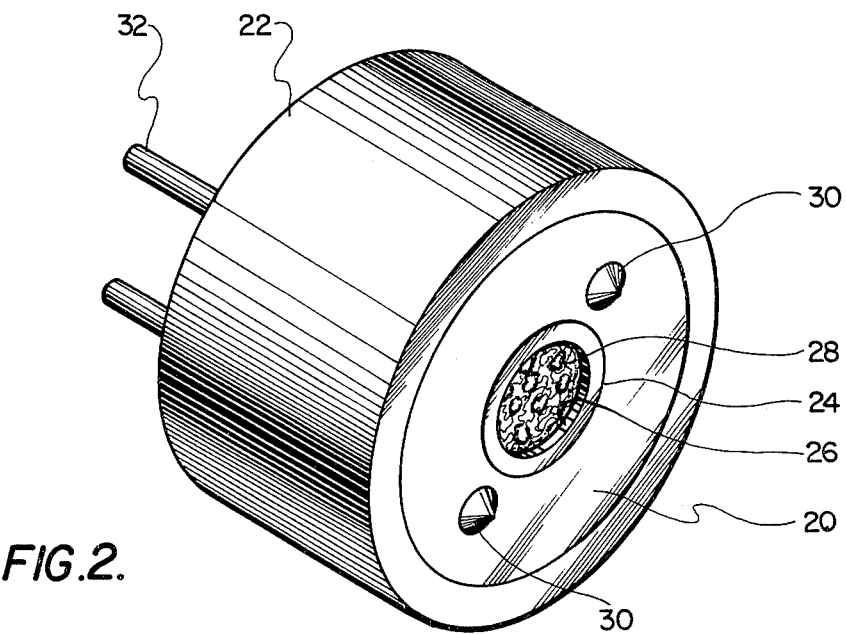
FIG. 2 is a perspective view of the working face of a barnacle cell according to the invention.

FIG. 2 is a perspective view of the working face of the electrochemical cell according to the present invention. This cell utilizes the same physical principles as the prior art cell shown in FIG. 1. The cell has an insulating body 20 made of Kel-F or other insulating material and a ring magnet 22 for holding the working face against the metal part being measured. If a nonmagnetic material were being measured, then a metal clamp would be used to hold the cell in place. A cavity 24 in body 20 is provided to house the anode and hold the electrolyte. A special ring seal 26 is positioned inside of cavity 24 to prevent leakage of electrolyte. The inside diameter of the ring seal determines the area of the metal being analyzed and is used in calculating the current density. In the cell shown in FIG. 2, the area inside ring seal 26 is 1.0 cm$^2$. A unique feature of the cell is the absorbent material or sponge 28 positioned within ring seal 26 to hold the electrolyte within cavity 24. Two spring loaded contacts 30 provide electrical contact with the metal being measured.

Figure 3:
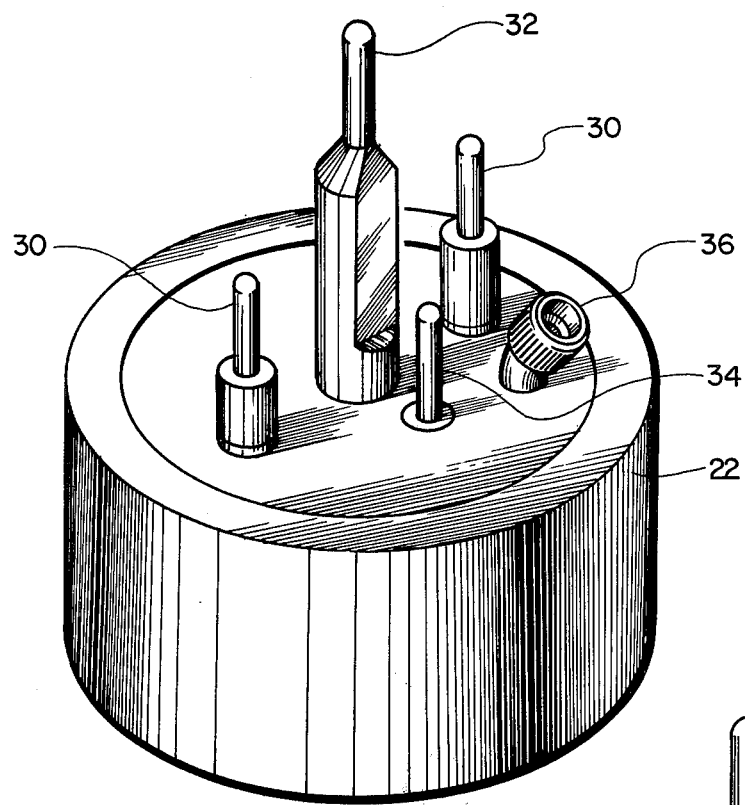
FIG. 3 is a perspective view of the top of the cell shown in FIG. 2.

FIG. 3 is a top view of the cell showing connectors 30, 32, 34. Connectors 30 are extensions of the contacts shown in FIG. 2. Connector 32 makes connection to the working anode inside cavity 24. Connector 34 also extends into cavity 24 and serves as a reference electrode for checking the performance of the cell.

Figure 4:
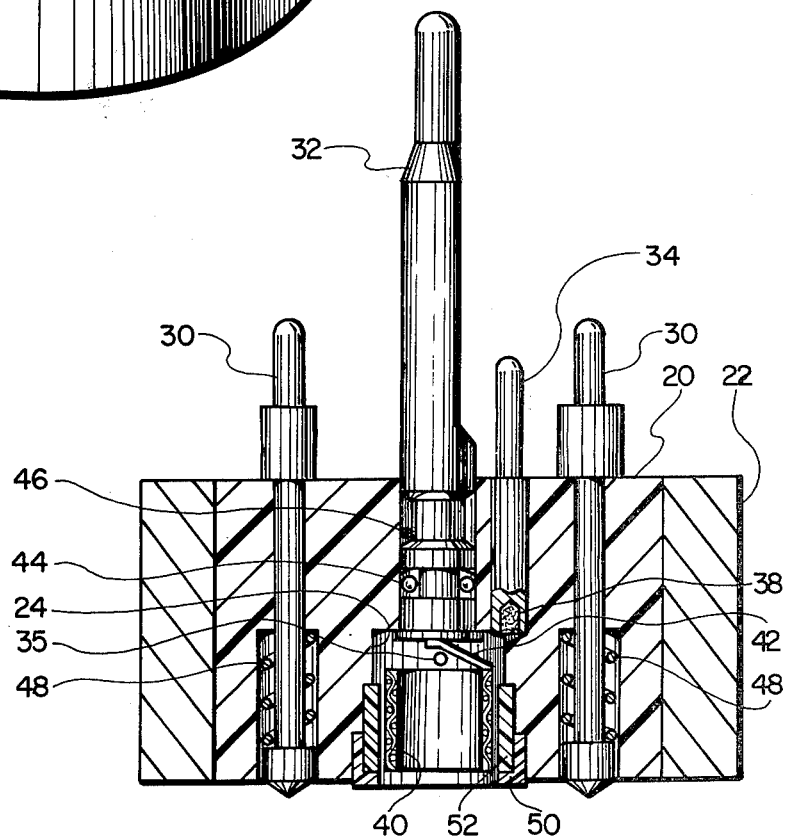
FIG. 4 is a cross-section of the cell shown in FIG. 2.

Cavity 24 is vented through a small hole (35 in FIG. 4). A threaded needle valve 36 extends from the back of the cell into hole 35 and can be used to open or close the vent.

FIG. 4 is a cross-section of the cell taken on the diameter through contacts 30. Reference electrode 34 has been rotated into the plane of the cross-section to show its structure. Reference electrode 34 is machined from a nickel rod that is pressed through insulating body 20 into cavity 24. Nickel oxide powder 38 is packed into a hole in the end of reference electrode 34. Working anode 40 is a cylindrical strip of porous nickel impregnated with nickel oxide. It is joined to anode connector 32 by means of a small tab 42 spot welded to electrode 32. Ring seal 44 permits vertical movement of connector 32 for positioning of anode 40 while still sealing chamber 24. Detent 46 limits the vertical movement of contact 32 to the length of its slot in contact 32.

When the cell is placed against the surface of the metal being measured, contacts 30 are pressed against the metal surface by springs 48. Ring seal 26 is pressed against the surface of the metal being measured and soft lip 50 seals the chamber. In the preferred embodiment shown in FIG. 4, ring seal 26 consists of an epoxy tube 52 with a silicone rubber lip 50 formed around its lower circumference. Rubber lip 50 protrudes about 0.003 inch below the working surface of the cell.

Figure 5:
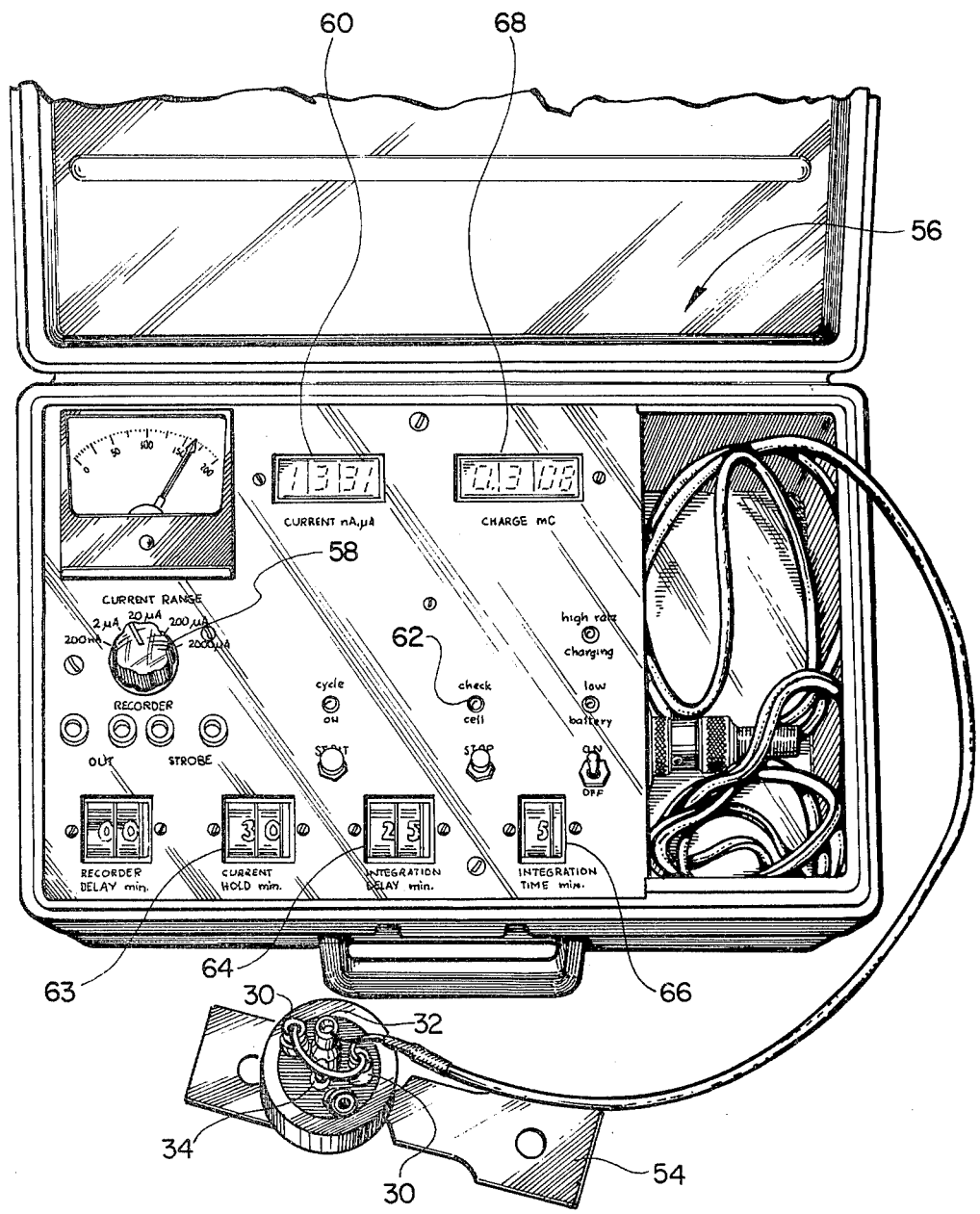
FIG. 5 shows the cell and electronic packaging during measurement of the hydrogen in a metal test specimen.

FIG. 5 shows the cell fastened to a metal test specimen 54 and connected to its electronic readout circuit.

Circuit 56 is reliable and compact and can be readily operated by shop personnel and laboratory technicians. It includes means for conveniently checking the preparedness of the cell. There are three electrical inputs to circuit 56: (1) from working anode connector 32, (2) from contacts 30, and (3) from reference electrode 34. In circuit 56, the voltage between reference electrode 34 and working anode 40 is compared to determine if anode 40 is depleted and to determine if the cell lacks sufficient electrolyte. If the voltage between reference electrode 34 and anode 40 exceeds 100 millivolts, then light emitting diode 62 is activated to warn the operator to check the cell. This monitoring occurs both before and during the measurement cycle. Additionally, if the cell has an inadequate amount of electrolyte, the resulting IR drop causes light emitting diode 62 to light.

Electronic readout circuit 56 is provided with current hold 63 which can be set for a particular time such as 30 minutes shown in FIG. 5. At the end of such set time, digital current indicator 60 holds the current reading. Circuit 56 also includes a timer for integrating the charge during selected time periods of a test cycle. As shown in FIG. 5, integration delay 64 is set to begin integration of the charge after 25 minutes. Integration timer 66 is set to integrate charge for five minutes following the 25 minute integration delay. The integrated charge after this time is shown as microcoulombs in digital charge indicator 68. The decimal point in 60 and 68 is determined by the setting of the current range 58. If preferred, digital current indicator 60 can be sealed to read directly in ppm.

Figure 6:
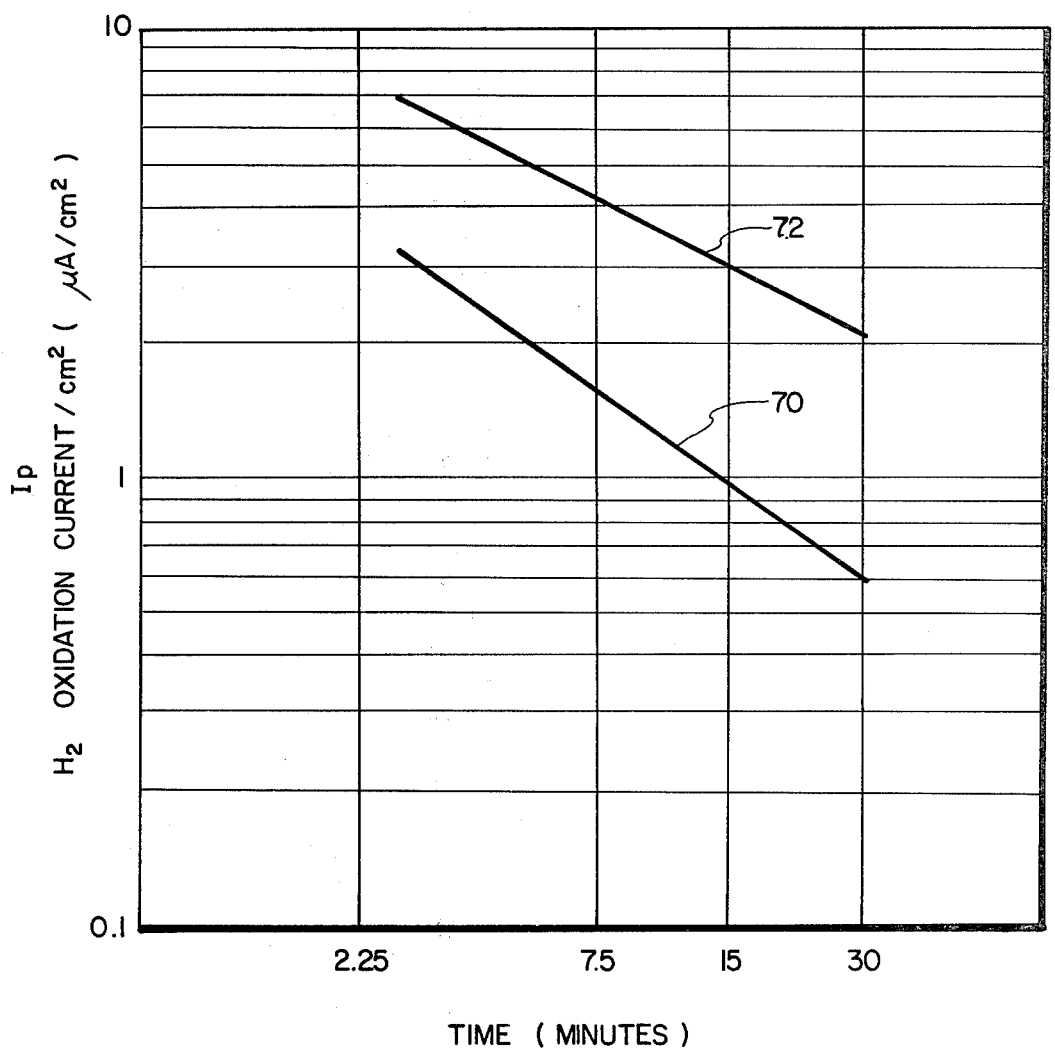
FIG. 6 is a log-log plot of hydrogen oxidation current vs time for an uncharged sample, and for a sample charged with hydrogen.

FIG. 6 shows test results 70, 72 obtained using the cell to measure the hydrogen content of a test specimen of 4340 steel (not charged with hydrogen) and of a similar specimen of 4340 which has been charged with hydrogen by making it the cathode in a NaOH-NaCN (10% each) solution. To obtain curves 70, 72 shown in FIG. 6, the hydrogen oxidation current per square centimeter, $I_p$, was measured continuously and recorded on a strip chart recorder. Curve 72 for the charged sample shows a higher oxidation current than curve 70 for the uncharged sample because of the higher hydrogen content of the charged sample. Actual hydrogen concentration of the two samples can be calculated from the diffusion equations as follows:

$$I = -zDF\left(\frac{\partial C}{\partial x}\right)_{x=L} \quad (1)$$

$$\frac{\partial^2 C}{\partial x^2} - \frac{1}{D}\frac{\partial C}{\partial t} = 0 \quad (2)$$

which are solved with the boundary conditions:

$$X = 0, t \geq 0, \frac{\partial C}{\partial x} = 0 \quad (3)$$
$$X = L, t > 0, C = 0$$
$$0 < X < L, t \leq 0, C = C_o$$

The time dependence of hydrogen oxidation current $I_p$ is found to be:

$$I_p = zFC_o\left(\frac{D}{\pi t}\right)^{\frac{1}{2}}\left[1 - e^{-L^2/Dt} + e^{-4L^2/Dt} + \ldots\right] \quad (4)$$

where z is the number of electrons involved in the oxidation reaction (z=1), F is the Faraday constant, D is the diffusion coefficient for hydrogen in a given metal, $C_o$ is the concentration of hydrogen in the metal, and L is the thickness of the foil.

For $e^{-L_2/DT} < <1$, Eq. 4 reduces to:

$$I_p = zFC_o \left(\frac{D}{\pi t}\right)^{\frac{1}{2}} . \tag{5}$$

Eq. 5 holds for a maximum measurement period $t_{max} = L^2/4D$. For 4340 steel (L=1 mm, D=2.5·10$^{-7}$ cm$^2$/sec) $t_{max} \sim 10^4$ sec. According to Eq. 5, the hydrogen concentration $C_o$ can be determined from a plot of log $I_p$ vs log t in the form:

$$\log I_p = \log \frac{zFD^{\frac{1}{2}}}{\pi^{\frac{1}{2}}} C_o - \frac{1}{2} \log t \tag{6}$$

as the intercept at t=1 sec, or can be calculated from the current measured at a given time t<$t_{max}$. Since at the beginning of the surface oxidation a certain amount of current is due to passivation of the steel, the hydrogen concentration has been calculated after 1800 sec (30 minutes) in the experiments described above. For a current density of 1 μA/cm$^2$, the hydrogen concentration $C_o$ is:

$C_o$=0.203 ppm.

Thus, for the uncharged sample (curve 70) which has a current density of 0.6 micro amps per cm$^2$ after 30 minutes, the hydrogen concentration is calculated to be 0.203×0.6 or about 0.12 ppm. For the charged sample (curve 72) which has a current density of 2.1 after 30 minutes, the hydrogen concentration is calculated to be 0.203×2.1 or about 0.43 ppm.

Although there are many factors which may affect the absolute values of the hydrogen concentration, numerous tests run using the cell of the present invention have shown that it is capable of determining the relative concentration of hydrogen in metal samples tested under similar conditions. When standardized conditions and suitable standards are utilized, the cell is a powerful tool for use in determining the hydrogen content of metal parts.

Sponge 28 has proven very helpful in holding electrolyte (0.2 N NaOH) within the cell cavity. Small amounts of a jell such as Agar jell (made 0.2 N NaOH) can be applied to the surface of the sponge to help provide 100% contact area and minimize leakage. Tests were run using cells without a sponge by carefully attaching the cell to the metal surface after filling it in the inverted position. After obtaining a seal, tests were run with the cell in its normal position. Comparison of these tests with similar tests run using a sponge showed that comparable results are obtained either with or without the sponge. Of course, the use of a sponge greatly simplifies placement of the cell against a metal surface and carrying out tests in the field.

Numerous variations and modifications may be made without departing from the present invention. For example, the working surface of the cell can be contoured to fit curved surfaces. In addition, alcoholic solutions of NaOH can be used for application at lower temperatures. Additionally, cathode material other than Ni/NiO can be used. Accordingly, it should be clearly understood that the form of the present invention described above and shown in the accompanying drawings is illustrative only and is not intended to limit the scope of the present invention.

What is claimed is:

1. An electrochemical cell for measuring hydrogen in metal, comprising:
    a body having a cavity with an open side;
    a vent extending from said cavity through said body to vent said cavity;
    a sponge in said cavity extending adjacent to said open side;
    a jell of electrolyte on said sponge adjacent said open side;
    seal means encompassing at least the portion of said cavity containing said sponge adjacent said open side, said seal means enclosing a predetermined area;
    an anode in said cavity for maintaining an oxidizing potential adjacent said open side;
    a contact electrode for making electrical contact with the metal when the cell is placed against the metal;
    means for measuring hydrogen oxidation current between said anode and said contact electrode;
    a reference electrode extending into said cavity; and
    means for measuring voltage between said reference electrode and said anode.

2. The cell as claimed in claim 1, wherein said anode comprises a nickel/nickel oxide anode.

3. The cell as claimed in claim 1, wherein said seal means comprises a tubular member extending into said cavity and having an elastomeric lip adjacent said open side for making sealing contact with the metal when said cell is placed against the metal.

4. An electrochemical cell for measuring hydrogen in metal, comprising:
    an insulating body having a cavity with an open side;
    a vent extending from said cavity through said body to vent said cavity;
    a tubular member extending into said cavity and having an elastomeric lip adjacent said open side for making sealing contact with the metal and for enclosing a predetermined area of the metal when the cell is against the metal;
    a sponge inside said tubular member substantially flush with said open side;
    a jell of electrolyte on said sponge adjacent said open side;
    a nickel/nickel oxide anode inside said tubular member for maintaining an oxidizing potential adjacent said open side;
    a spring loaded contact electrode extending out of said body on said open side for making electrical contact with the metal when the cell is placed against the metal;
    means for measuring hydrogen oxidation current between said anode and said contact electrode;
    a reference electrode extending into said cavity;
    means for measuring voltage between said reference electrode and said anode; and
    a vent extending from said cavity through said body.

5. The cell as claimed in claim 4 including a magnet fastened to said insulating body for holding said cell to the metal.

* * * * *

UNITED STATES PATENT AND TRADEMARK OFFICE
CERTIFICATE OF CORRECTION

PATENT NO. : 4,221,651

DATED : September 9, 1980

INVENTOR(S) : Florian B. Mansfeld and David K. Roe

It is certified that error appears in the above-identified patent and that said Letters Patent are hereby corrected as shown below:

ABSTRACT, line 5, change "an anode" to --- a cathode ---; and in lines 11, 18, and 19, change "anode" to --- cathode ---.

Column 1, line 27, change "proposed" to --- demonstrated ---.

Column 2, lines 6 and 63, change "An anode" to --- A cathode ---; in lines 14, 21, 22, 24, and 26, change "anode" to --- cathode ---; in line 58, delete "proposed"; and in lines 64-65, delete "Note that the design in FIG. 1 has never been used experimentally in the field".

Column 3, line 1, change "Anode" to --- Cathode ---; in lines 4, 23, 52, and 55, change "anode" to --- cathode ---; in line 37, change "working anode" to --- cathode ---; and in lines 50-51, change "Working anode" to --- Cathode ---.

Column 4, lines 5 and 8, change "working anode" to --- cathode ---; and in lines 9 and 11, change "anode" to --- cathode ---.

Column 6, line 19, change "an anode" to --- a cathode ---; and in lines 24, 27, 28, 29, 49, 57, and 60, change "anode" to --- cathode ---.

Signed and Sealed this

Tenth Day of March 1981

[SEAL]

Attest:

RENE D. TEGTMEYER

*Attesting Officer*    *Acting Commissioner of Patents and Trademarks*